(12) United States Patent
Alsheikh

(10) Patent No.: US 11,844,912 B2
(45) Date of Patent: Dec. 19, 2023

(54) METHOD FOR VISUALIZING A CATHETERIZATION GUIDEWIRE

(71) Applicant: Thabet Alsheikh, Pensacola, FL (US)

(72) Inventor: Thabet Alsheikh, Pensacola, FL (US)

( * ) Notice: Subject to any disclaimer, the term of this patent is extended or adjusted under 35 U.S.C. 154(b) by 791 days.

(21) Appl. No.: 16/549,015

(22) Filed: Aug. 23, 2019

(65) Prior Publication Data

US 2021/0052860 A1 Feb. 25, 2021

(51) Int. Cl.
| | |
|---|---|
| *A61M 25/09* | (2006.01) |
| *A61B 5/00* | (2006.01) |
| *A61M 25/01* | (2006.01) |
| *A61B 18/00* | (2006.01) |
| *A61B 5/287* | (2021.01) |

(52) U.S. Cl.
CPC .......... *A61M 25/09* (2013.01); *A61B 5/6851* (2013.01); *A61M 25/0105* (2013.01); *A61B 5/287* (2021.01); *A61B 2018/00077* (2013.01); *A61B 2018/00083* (2013.01); *A61M 2025/09133* (2013.01)

(58) Field of Classification Search
CPC ............. A61M 25/09; A61M 25/0105; A61M 2025/09133; A61M 2025/09166; A61M 2025/09083; A61B 5/6851; A61B 5/06; A61B 2034/2051
See application file for complete search history.

(56) References Cited

U.S. PATENT DOCUMENTS

| | | | | |
|---|---|---|---|---|
| 8,340,751 B2 * | 12/2012 | Markowitz | ............ | A61B 5/287 600/523 |
| 8,764,683 B2 * | 7/2014 | Meller | ................ | A61B 5/6851 600/585 |
| 9,031,647 B2 * | 5/2015 | Maskara | ................ | A61N 1/056 607/9 |
| 2015/0080762 A1 * | 3/2015 | Kassab | ............ | A61M 25/0017 600/585 |

* cited by examiner

*Primary Examiner* — Devin B Henson
(74) *Attorney, Agent, or Firm* — J. Wiley Horton

(57) ABSTRACT

A guide wire configured for use with existing catheter mapping and navigation systems. The guide wire is made of electrically conductive material and coated in an electrically insulating material. An uncoated region is provided near the guide wire's distal tip. This uncoated region forms a conductive path between the metallic components of the guide wire and the surrounding tissue. The uncoated region effectively becomes an electrode for use in prior art mapping and navigation systems. The mapping and navigation system determines the position of the uncoated region.

20 Claims, 17 Drawing Sheets

METHOD FOR VISUALIZING A CATHETERIZATION GUIDEWIRE

CROSS-REFERENCES TO RELATED APPLICATIONS

Not Applicable

STATEMENT REGARDING FEDERALLY SPONSORED RESEARCH OR DEVELOPMENT

Not applicable

MICROFICHE APPENDIX

Not applicable

BACKGROUND OF THE INVENTION

1. Field of the Invention

This invention relates to the field of medical products. More specifically, the invention comprises a guide wire that can be detected and depicted by existing catheter navigation and mapping systems.

2. Description of the Related Art

The present invention pertains to a guide wire that can be used to introduce a catheter. The specific examples that are described in detail pertain to cardiac catheterization. However, the reader should bear in mind throughout this disclosure that the invention has broader applications.

FIG. 1 depicts a process of cardiac catheterization in a very simplistic form. Access to the human circulatory system is gained through entry site 12. There are many known processes for gaining access. In the example shown, access to the left side of the heart is the objective. A Seldinger needle is inserted into the right femoral artery. A guide wire is inserted through the Seldinger needle and advanced toward the heart. As those skilled in the art will know, guide wires typically allow the physician to deflect the distal tip a desired amount and rotate the guide wire assembly as a whole. These functions—in combination—allow the physician to properly route the advancing guide wire.

The reader should note that the guidewire in the depiction of FIG. 1 has a much larger diameter than would actually be the case. The largest portion of a guide wire typically has a diameter that is less than 2 mm. It is difficult to depict the actual dimensions of such an object and so an enlarged version is shown in FIG. 1.

After access is provided to the right femoral artery, the guide wire is routed through the right exterior iliac artery, through the right common iliac artery, and into the abdominal aorta. From that point the physician routes the guide wire up the descending aorta, through the aortic arch, and into the heart itself.

Fluoroscopy is traditionally used to visualize the position of the guide wire as it is advanced. Guide wires are often made of radio-opaque materials so they may be visualized using a fluoroscope. Because of the fact that radiocontrast dye is frequently injected for cardiac artery circulation studies, a fluoroscope is often present in the cardiac catheterization surgical suite and this makes the use of a fluoroscope for directing the guide wire convenient. The physician must exercise care to both select the proper path of the guide wire and to avoid damaging any vessel walls. This requires period activation of the fluoroscope and continued activation for intervals of several seconds.

The fluoroscope provides a two-dimensional image. Most such machines allow reorientation so that the physician can "shoot" a second plane (most often orthogonal to the original plane). The physician can rotate the guide wire and selectively deflect its tip while watching the fluoroscopic images on a monitor. This allows the physician to skillfully advance the guide wire to a desired location.

FIG. 2 provides a simplified cutaway view of the human heart 16. In this procedure the physician wishes to insert a catheter into the left ventricle. This may be done for various reasons. One common reason is to create an electrical map of the heart so that ablation techniques can be used to treat an arrhythmia. In the depiction of FIG. 2, the region proximate the aortic valve has been cut away to aid visualization. The physician advances guide wire 14 up descending aorta 32, through aortic arch 20 and down through the aortic valve into left ventricle 24 (The region of the aortic valve is within the cut away and not shown in the view). Note that the guide wire is again depicted as having a much larger diameter than is actually the case.

Once the guide wire is resting in the desired position, the physician advances catheter 18 over the guide wire. The catheter has a hollow center allowing it to pass over the guide wire with little resistance. Once the catheter is in place, the physician typically retracts and removes the guide wire. FIG. 3 shows catheter 18 in an operative position with the guide wire removed.

In most cases the physician is able to rotate catheter 18 and independently vary the amount of deflection present in its distal end. Multiple electrodes 34,36,38,40 are located along the catheter. In the example shown the electrodes are configured to perform multiple functions. First, they act as sensors to measure electrical activity in a particular part of the heart they touch. Second, they provide navigation and mapping functions (which will be explained subsequently). Third, one or more of the electrodes provides a cauterization function so that scar tissue can be created along the heart wall—thereby altering the heart's electrical pathways.

Prior Art Catheter Navigation and Mapping Systems

In the past two decades systems have evolved that can accurately determine the position of a catheter within the human body ("navigation and mapping" systems). There are now several different types of these systems. FIGS. 4 and 5 illustrate one particular type of navigation and mapping system. The reader should bear in mind that the present inventive method and hardware can be adopted for use with many different types of navigation and mapping systems and are not limited to any particular type.

FIG. 4 illustrates the placement of external electrodes on the human body for use in determining the position of a catheter inside the body. The basic concept is to pass a small electrical current through the body and then measure a voltage between an electrode on a catheter inside the body and a reference electrode placed on the outside of the body.

An arbitrary coordinate system is created for the body. As the present example concerns cardiac catheterization, it is convenient to center this coordinate system approximately on the heart. Still looking at FIG. 4, the origin of this coordinate system lies at the intersection of the X-axis, the Y-axis, and the Z-axis. At a first time a small electrical current is passed from electrode Y1 (reference numeral 52) to electrode Y2 (reference numeral 54). During this time a catheter is lying within the body (having been introduced through entry site 12). The catheter includes an electrode. A measurement system is used to measure an electrical potential between the electrode on the catheter and reference electrode 46.

In the exemplary system an assumption is made that the resistance of the human body is linear. A thought experiment then serves to illustrate the very basic operational concept of the navigation and mapping system. In this thought experiment one should assume that the catheter electrode can be placed anywhere inside the volume of the patient's body (Anatomy obviously precludes this possibility for most locations, but it is useful for the thought experiment). If current is passed from electrode 52 to electrode 54, then the measured voltage between the catheter electrode and the reference electrode will be least at the emitter electrode and it will increase as one travels away from the emitter electrode and toward the collector electrode. This is true because the electrical current must travel through an increasing distance before reaching the electrode on the catheter. Increasing distance means increasing resistance and consequently an increasing voltage drop. The measured voltage may therefore be correlated to a position along the Y-axis.

The same operation can be performed for the X-axis and the Z-axis. For X-axis position gathering a current is sent between electrode X1 (reference numeral 48) and electrode X2 (reference numeral 50). For Z-axis position gathering a current is sent between electrode Z1 (reference numeral 56) and electrode Z2 (reference numeral 58).

These three imposed currents can be multiplexed in time. It is also possible, however, to simultaneously impose all three axes by using different frequencies for an alternating current. As an example, the X-Axis electrodes can operate at 30 kHz, while the Y-Axis electrodes operate at 31 kHz and the Z-axis electrodes operate at 32 kHz. The frequency selection is somewhat arbitrary. However, one should bear in mind that a conventional 12-lead electrocardiogram ("ECG") array will often be present on the patient. The frequencies selected should not interfere with the ECG data collection and should not interfere with each other. A suitable notch filter can be used for each axis so that the voltage measuring equipment does not "see" the other axes.

FIG. 5 provides a schematic depiction of the type of processing equipment that is used to create a catheter navigation and mapping display. Patient 10 is depicted as a dashed outline with the previously described coordinate reference system superimposed thereon. Catheter 18 includes a tip electrode 34 and a second electrode 36 a known distance "D" away. Reference electrode 120 provides the reference for the voltage measured at tip electrode 34 and second electrode 36.

Multiplexer 60 is a digital switching device that is controlled by processor 80. It samples the appropriate electrodes and feeds the signals to the processing channel for the X-axis, the Y-Axis, and the Z-axis. For instance, multiplexer 60 can feed a measured voltage between electrode 34 and reference electrode 120 to all three channels.

In the upper channel shown in the view, X filter 62 is a narrow band pass filter set to pass the 30 kHz signal used for the X-axis and exclude the 31 kHz and 32 kHz signals used for the Y-axis and Z-axis. Likewise, Y-filter 64 is sent to pass a 31 kHz signal and Z-filter 66 is set to pass a 32 kHz signal. Amplifiers 68,70,72 amplify the signal emerging from the band pass filters. Artifact removal processors 74,76,78 remove errors in the signals caused by respiration and contractions (explained in more detail subsequently).

Processor 80 takes in the data and transforms it into a visual depiction of the location and orientation of the catheter within the patient's body. This information is then rendered on display 82. The physician can thereby see the location and orientation of the catheter in real-time on display 82. There are of course some processing delays but these are generally less than 50 milliseconds and are therefore not perceptible. In this example processor 80 also controls current driver 84, which transfers the current signals to electrodes 48-58.

The measured voltages for each of the three axes can be converted into location values as follows: Assuming that resistance across the body is uniform, the three different measured voltage values for tip electrode 34 (voltages resulting from current applied in the X direction, the Y direction, and the Z direction) provide unique x, y, and z position data for the tip electrode. The equations (based on Ohm's Law) may be written as follows:

$$V_x = ax$$

$$V_y = by$$

$$V_z = cz$$

The constants (a, b, and c) are unknowns which must be solved via calibration. In this example, it is quite helpful to have voltage measurements taken from a second electrode 36 that is a known distance "D" from first electrode 34. Each of these two electrodes produces a voltage for each of the three currents (X, Y, and Z) imposed on the patient's body. This fact produces the following sets of equations:

$$V_{x1} = ax_1,\ V_{y1} = by_1,\ V_{z1} = cz_1$$

$$V_{x2} = ax_2,\ V_{y2} = by_2,\ V_{z2} = cz_2$$

The total distance "D" between the two electrodes 34,36 is known, and this fact helps to solve for the unknown constants. One can express the distance between the two electrodes as follows:

$$\Delta x = x_2 - x_1,$$

$$\Delta y = y_2 - y_1,\text{ and}$$

$$\Delta z = z_2 - z_1$$

Pythagoras' theorem then provides:

$$(\Delta x)^2 + (\Delta y)^2 + (\Delta z)^2 = D^2$$

One may easily determine the voltage differences between the two electrodes 34,36, since these are just the difference between two measured values, written as:

$$\Delta V_x = V_{x2} - V_{x1},$$

$$\Delta V_y = V_{y2} - V_{y1},\text{ and}$$

$$\Delta V_z = V_{z2} - V_{z1}$$

According to Ohm's Law, the voltage differences are also related to the unknown constants as follows:

$$\Delta V_x = a \Delta x,$$

$$\Delta V_y = b \Delta y,\text{ and}$$

$$\Delta V_z = c \Delta z$$

These expressions may be algebraically rewritten as:

$$\Delta x = \Delta V_x / a,$$

$$\Delta y = \Delta V_y / b,\text{ and}$$

$$\Delta z = \Delta V_z / c$$

Substituting the rewritten equations into Pythagoras' theorem then yields:

$$\left(\frac{\Delta V_x}{a}\right)^2 + \left(\frac{\Delta V_y}{b}\right)^2 + \left(\frac{\Delta V_z}{c}\right)^2 = D^2$$

This equation exists for any fixed position of the two electrodes 34,36 and corresponding measured voltages of the two electrodes. The voltage differences are determined from the measurements of voltage at the two electrodes. The distance "D" is known (D does vary slightly with the curvature of the end of the guide wire, but this variation is minimal and can be safely ignored).

The rewritten equation includes three unknowns that need to be determined (a,b, and c). The reader should recall that these unknowns are assumed to be constant for all positions of the electrodes within the body. It is therefore possible to obtain sample voltages at three different guide wire positions and thereby obtain three independent equations. Using these three independent equations the three unknowns can be determined using basic principles of linear algebra.

One could create a "calibration step" in which the physician moves the catheter to three different locations and then stops while voltage readings are taken. In reality such a step is unnecessary. The sample rate of the processing electronics (such as shown in FIG. 5) is typically 60 Hz or greater. The physician is constantly maneuvering and repositioning the catheter within the patient. Thus, the prior art navigation and mapping systems can periodically create a calibration step that refines and updates the value for the constants a, b, and c. This process is invisible to the physician.

Once the constants are known the measured voltage at each electrode 34,36 can be converted directly into a linear position along the reference axis. This process is done for each axis (X, Y, and Z) and the position of each electrode within the body is thereby determined. The process can be completed for 2, 3, 4, or more electrodes positioned along the catheter. Computer graphics processing is then used to pass a smooth curve through each of the computed points and then create a three-dimensional graphical depiction of the catheter that can be displayed on a monitor.

Returning to FIG. 3, the graphical depiction of catheter 18 can be made to appear like the depiction in this view. The multiplexer in the controlling electronics typically switches off the navigation and mapping functions as part of each cycle and uses the same electrodes to measure the electrical activity of the heart. The physician "sweeps" the catheter around and thereby builds a set of coordinate points that define the volume the catheter is presently within (the left ventricle in the example shown). The computer graphics processing then uses these sets of measured points to create a sophisticated three-dimensional depiction of the anatomy in the vicinity of the catheter. The display often gives the physician the ability to reorient the view, zoom in and out, pan, etc.

Artifact Removal

Artifact removal is significant to the creation of an accurate geometric depiction of the catheter and the surrounding anatomy. In this context the term "artifact" refers to an unwanted distortion in the geometry data. There are two main sources of artifacts for navigation and mapping systems. The first is respiration and the second is cardiac contraction (normal heart functions continue during the catheterization procedure).

Cardiac contraction phenomena are eliminated using the processing software. Many individual geometric points are created and stored as the catheter is swept around. The software assumes that the outermost points within a particular volume represent the heart chamber in a relaxed state. These are used to define the volume. A smooth surface is then passed through this outer "shell" of harvested points.

Respiration is a more complex phenomenon. Respiration obviously causes displacement of the points determined. It also alters the values calculated for the constants (a, b, and c). This results from the fact that the electrical resistance of the lung tissue changes through each respiration cycle. The actual current paths through the lungs change with respiration. In addition, the resistivity of oxygenated blood is significantly altered from the deoxygenated state. One need only visualize the location of the heart with respect to the lungs to realize that these phenomena will be quite significant in introducing location errors for heart catheterization procedures.

Early systems used a low pass filter to reduce the effect of respiration artifacts. However, as respiration itself is a low frequency phenomenon, the filter required had to be in the range of 0.25 Hz (respiration itself being in the range of 0.1-0.2 Hz). Using a filter with a "roll-off" set this low compromises the ability to distinguish contraction phenomena and other significant phenomena.

More recent systems have mitigated the effects of respiration errors using two distinct but complimentary approaches. In the first approach the 3 pairs of current-passing electrodes are also used as voltage sampling electrodes. In the prior example, the 3 pairs were operated simultaneously by using three distinct emitter frequencies (such as 30 kHz, 31 kHz, and 32 kHz). In the more recent approach the same frequency is used for all but they are multiplexed in time. Each pair is operated for a short "burst." As an example, the X-axis pair 48, 50 can be operated while the Y-Axis pair and the Z-Axis pair are switched off. However, during this same interval, the Y-Axis electrodes and the Z-axis electrodes can be used to take voltage samples and thereby create additional data points. In addition, because these data points are known to be on the body's exterior surface, they are useful in tracking the expansion and contraction motions that indicate a particular point in the respiration cycle.

In the second approach, a known anatomical reference can be used. During catheterization the physician can maintain a particular catheter electrode at a known and fixed reference. As an example, the physician can place the catheter proximate an intra-cardiac reference for a period sufficient to encompass multiple respiration cycles. The mapping software then uses this reference to measure and remove the respiration artifact.

The use of these improved mapping and navigation algorithms produce a very accurate depiction of a cardiac catheter. Position error for the individual electrodes is now down to just a few millimeters. The accurate depiction of the catheter position and cardiac anatomy allow the physician to very accurately perform cardiac catheterization procedures. Additional details regarding these prior art mapping and navigation systems are disclosed in U.S. Pat. Nos. 5,983,126 and 7,263,397, which are hereby incorporated by reference.

Guide Wires for Catheterization

As explained previously, before a catheter can be introduced, a guide wire must be passed through the patient's vessels to the proper location. Guide wires assume a wide variety of forms. FIGS. 6-7 illustrate one type of prior art guide wire.

FIG. 6 shows two portions of the same guide wire. Proximal portion 94 includes tubular extension 86 and handle portion 88. These components remain outside the patient during use. Distal portion 96 is inserted into the body and advanced through the vessels. The guide wire includes two main components. These are core wire 90 and helical coil 92. Core wire 90 in this example is made from stainless steel. The core wire diameter in the proximal portion is about 0.20 mm (0.008 inches). The length of the proximal portion is about 140 cm.

The helical coil in this example is made of a platinum alloy. A first example is an alloy containing 92% platinum by mass and 8% tungsten by mass. A second example is an alloy containing 70% platinum by mass and 30% gold by mass. The cross-sectional diameter of the helical coil is about 0.05 mm (0.002 inches).

As can be seen, the pitch of the helix changes over different portions of the guide wire. The overall diameter of the helix increases in end region 98. Tip 100 lies at the extreme distal end of the guide wire. The operation of this guide wire will be familiar to those skilled in the art. There are three degrees of freedom that are significant to the physician: (1) end portion 98 can be deflected laterally by turning the helix with respect to the core wire, (2) The guide wire as a whole can be turned by turning the helix and the guide wire in unison, and (3) The guide wire can be advanced and withdrawn in the longitudinal direction. These three degrees of freedom allow the successful manipulation and placement of the guide wire.

FIG. 7 shows a further-magnified depiction of various significant portions of the guide wire. In the vicinity of the handle region the helical coil 92 is connected to the core wire 90 by bonds 101, 104. Along most of its length, however, the helical coil is free to rotate with respect to the core wire. The pitch of the helix grows larger over the middle section of the guide wire before shrinking again as the helix approaches end portion 98. The core wire diameter tapers from 0.20 mm in the handle region, to 0.12 mm in the mid portion. The diameter tapers again through tapered portion 106 to an ultimate diameter of about 0.05 mm near tip 100. This end portion of the core wire is then flattened to form flattened portion 108. The very distal end of flattened portion 108 is connected to tip 100 via bond 110. The distal end of the helical coil is likewise connected to tip 100—via bond 112.

Flattened portion 108 of the core wire is able to freely blend without undergoing plastic deformation. The reader will note how the overall diameter of the helical coil expands significantly proximate the tip. End portion 98 is soft and floppy. The physician is able to bend the end portion a desired amount by turning the helical coil with respect to the core wire. The physician is able to orient the guide wire by turning the assembly of the core wire and the helical coil together. This functionality allows the physician to direct the guide wire into a particular vessel branch and advance it as desired. The guide wire is provided with a lubricious coating to aid its passage through the body. One exemplary lubricious coating is 1 mil thick TEFLON. Another exemplary coating is MDX4 silicone. These coatings are provided over all the external surfaces of the guide wire. They reduce friction between all portions of the guide wire and a vessel wall. The coatings also provide electrical isolation between the guide wire and the surrounding tissues, though this is not necessarily an intended effect. U.S. Pat. No. 5,147,317 discloses more detail concerning this type of guide wire and is hereby incorporated into this disclosure by reference.

A guide wire such as depicted in FIGS. 6 and 7 has varying degrees of radio opacity. The significant areas—such as the area of end portion 98—are highly opaque. This allows the physician to visualize the advancing guide wire using a fluoroscope. As mentioned previously, however, the use of a fluoroscope causes unwanted radiation exposure. It would be advantageous to provide a guide wire that can use the electronic navigation and mapping functions now found in catheters. The present invention provides such a solution.

BRIEF SUMMARY OF THE PRESENT INVENTION

The present invention comprises a guide wire configured for use with existing catheter mapping and navigation systems. The guide wire is made of electrically conductive material and coated in an electrically insulating material. An uncoated region is provided near the guide wire's distal tip. This uncoated region forms a conductive path between the metallic components of the guide wire and the surrounding tissue.

The uncoated region effectively becomes an electrode. This electrode is connected to a processor in a mapping and navigation system—preferably by attaching an electrical lead to an uninsulated portion of the guide wire lying outside the patient's body. The mapping and navigation system determines the position of the uncoated region proximate the guide wire's distal tip. This position is preferably displayed on a monitor so that a physician can visualize the location of the guide wire's distal tip.

The inventive guide wire optionally includes a secondary electrode proximate the uncoated region proximate the distal tip. This secondary electrode is also connected to the processor in the mapping and navigation system. The mapping and navigation system then determines and displays the position of the secondary electrode.

Figure 1:
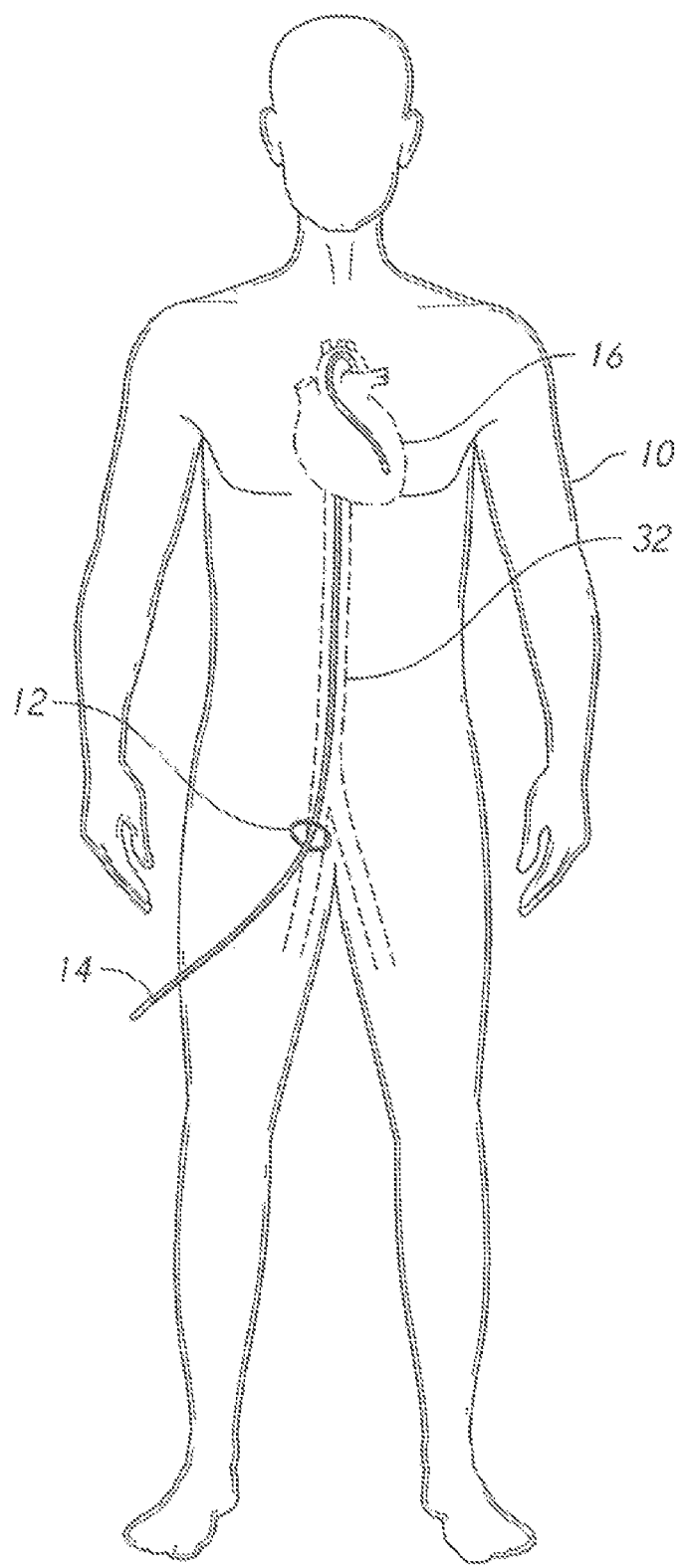
FIG. 1 is a schematic view, showing a simplistic depiction of a path of a guide wire used in cardiac catheterization.
Figure 2:
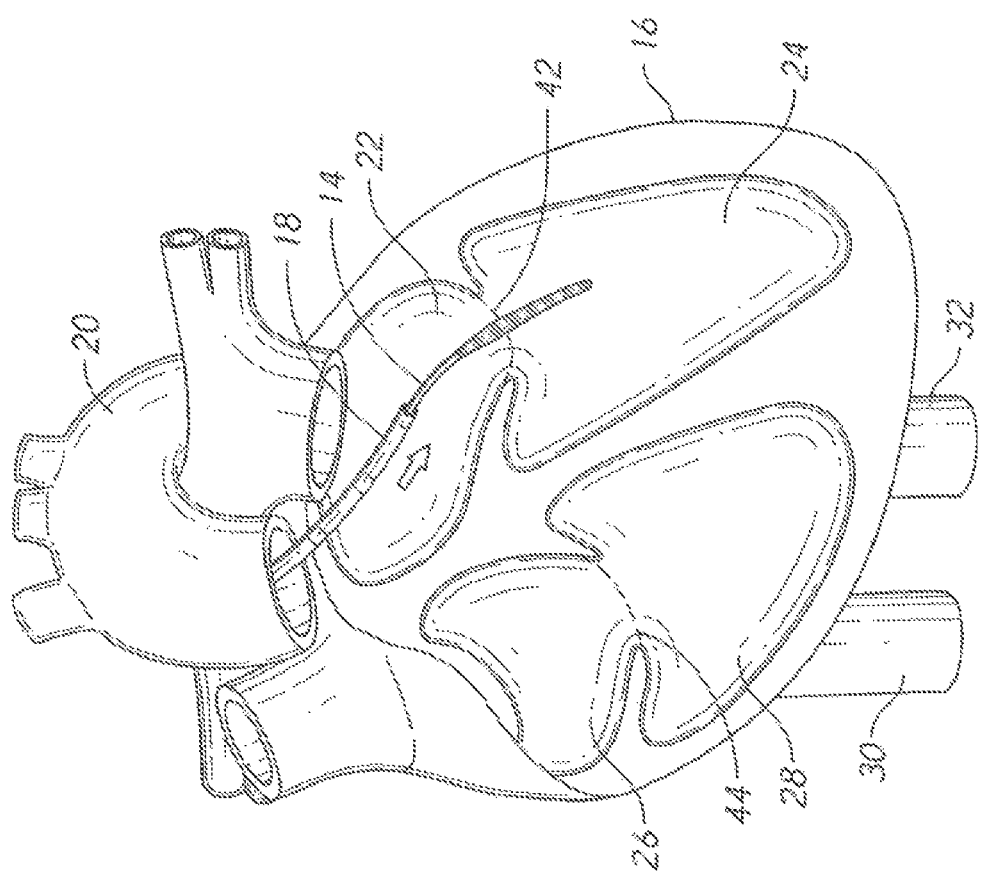
FIG. 2 is a perspective view with a cutaway, showing the use of a guide wire to place a catheter.
Figure 3:
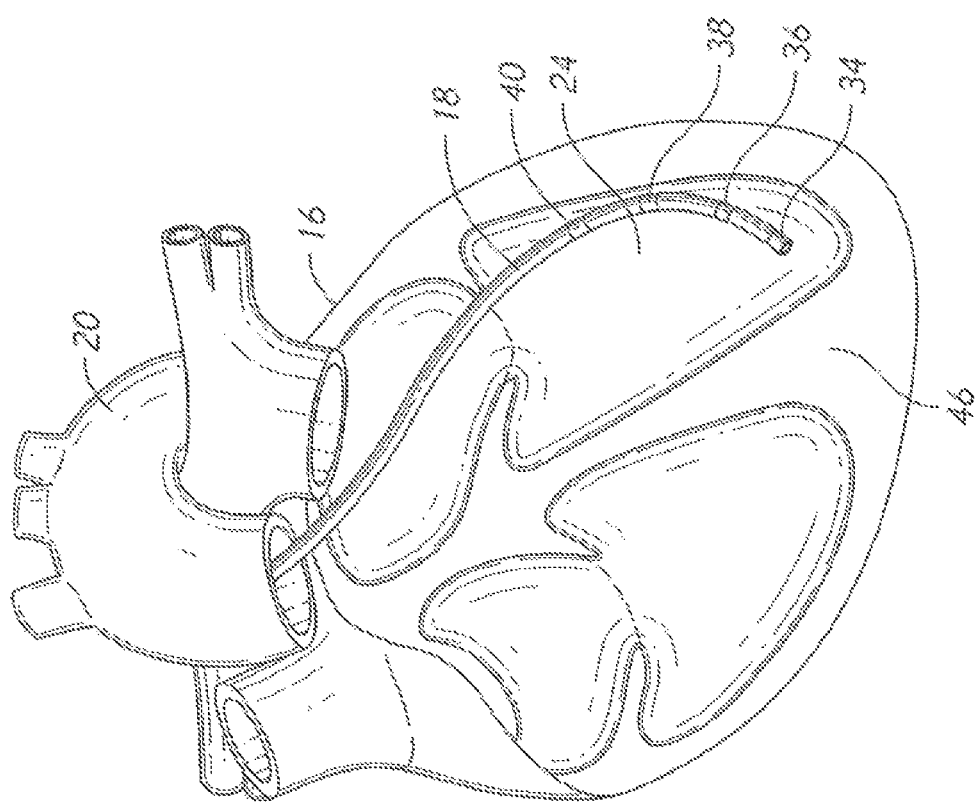
FIG. 3 is a perspective view with a cutaway, showing the use of a cardia catheter.
Figure 4:
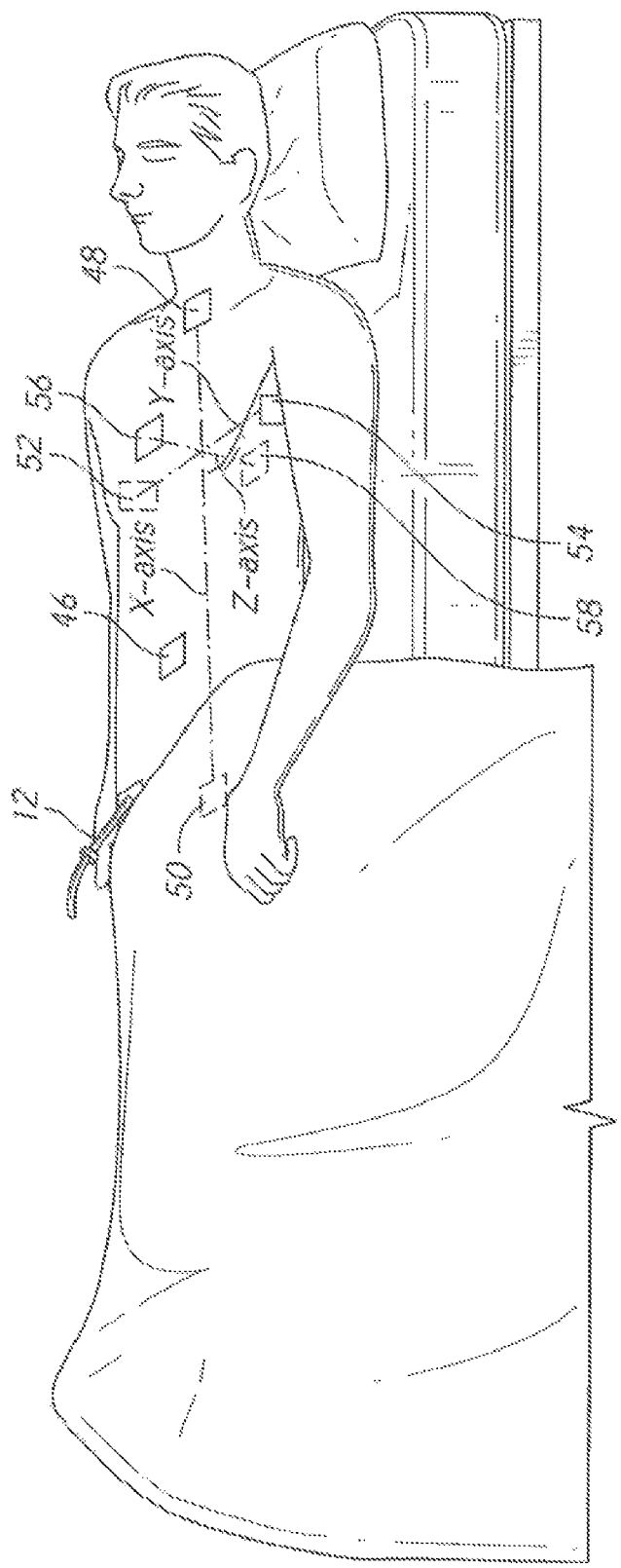
FIG. 4 is a perspective view, showing the placement of external electrodes used in a catheter navigation and mapping system.

REFERENCE NUMERALS IN THE DRAWINGS 10 patient
12 entry site
14 guide wire
16 heart
18 catheter
20 aortic arch
22 left atrium
24 left ventricle
26 right atrium
28 right ventricle
30 inferior vena cava
32 descending aorta
34 electrode
36 electrode
38 electrode
40 electrode
42 mitral valve
44 tricuspid valve
46 reference electrode
48 electrode X1
50 electrode X2
52 electrode Y1
54 electrode Y2
56 electrode Z1
58 electrode Z2
60 multiplexer
62 X filter
64 Y filter
66 Z filter
68 X amplifier
70 Y amplifier
72 Z amplifier
74 X artifact processor
76 Y artifact processor
78 Z artifact processor
80 processor
82 display
84 current driver
86 tubular extension
88 handle portion
90 core wire
92 helical coil
94 proximal portion
96 distal portion
98 end portion
100 tip
102 bond
104 bond
106 tapered portion
108 flattened portion
110 bond
112 bond
114 coating
116 exposed portion
118 electrical lead
119 electrical lead
120 reference electrode
122 monitor
124 patient depiction
126 tip location depiction
128 route history depiction
130 touch-based menu
132 aortic arch depiction
134 descending aorta depiction
136 insulating sheath
138 exposed region
140 3D depiction
142 secondary electrode
144 insulated lead

DETAILED DESCRIPTION OF THE INVENTION

Figure 8:
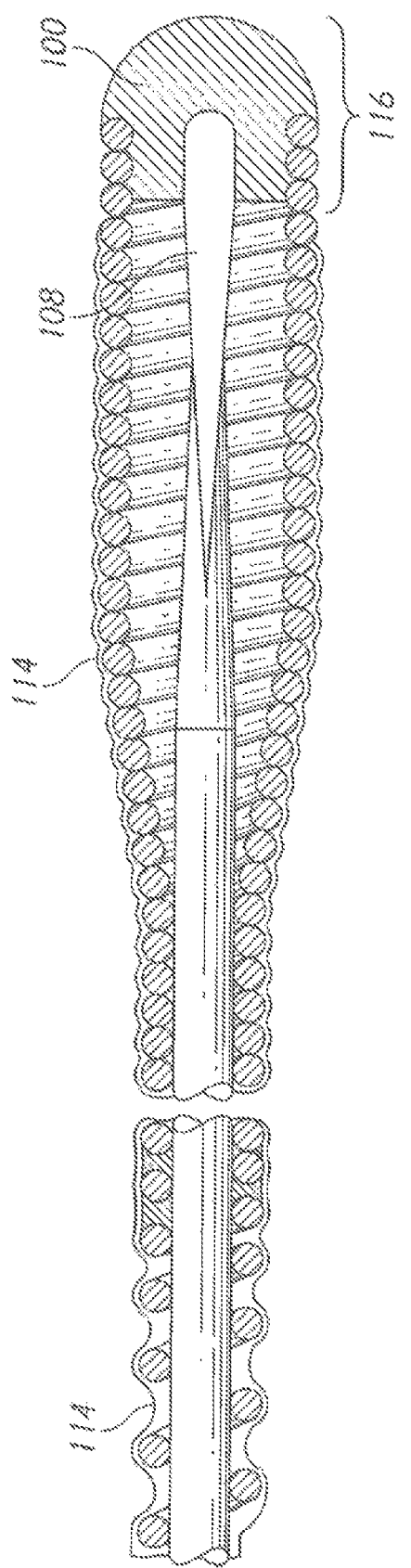
FIG. 8 is a partial sectional view, showing the end portion of a guide wire made according to the present invention.

FIG. 8 shows a guide wire modified according to the present invention. Coating 114 exists over the entire length of the guide wire that is intended to lie within the patient's body during use—with one exception. The coating selected provides electrical isolation between the conductive components of the guide wire and the surrounding tissue. In addition, the coating selected must provide suitable protection of the patient's vessels. The coating is preferably soft and slick. Suitable examples—as stated previously—are TEFLON and MDX4 silicone.

Exposed portion 116 is free from any coating. Thus, it provides a low-resistance electrical path between the conductive components of the guide wire (the tip, the core wire, and the helical coil) and the surrounding tissues of the patient. In the example shown the exposed portion is provided on the very tip of the guide wire. This need not always be the case. In other embodiments the exposed portion can be a band that is located some distance away from the tip.

The exposed portion can be created in different ways, and the invention is not limited to any particular method of creation. As a first example, the entire guide wire can be coated via a dipping or spraying operation. Exposed portion 116 is then created by removing the coating in that area. The coating can be removed via abrading, peeling, or chemically stripping the coating.

As a second example, a mask can be applied to exposed portion 116 before the coating is added to the balance of the guide wire. The mask is removed once the coating has set. As a third example the entire assembly can be dipped into a vessel containing the coating in a liquid state, while exposed portion 116 is held free of the coating. Other possibilities exist as well.

Tip 100 is made of a conductive material, such as stainless steel, The bond between tip 100 and flattened portion 108 is preferably a conductive bond. Such a bond can be made via brazing or welding the components together. Such a bond can also be made using conductive adhesive—such as a conductive fiber-filled epoxy. The result is the creation of a low-resistance electrical path from exposed portion 116 back to the core wire. The core wire then creates a low-resistance electrical path all the way to the proximal end of the guide wire—with the proximal end remaining outside the patient's body.

Figure 9:
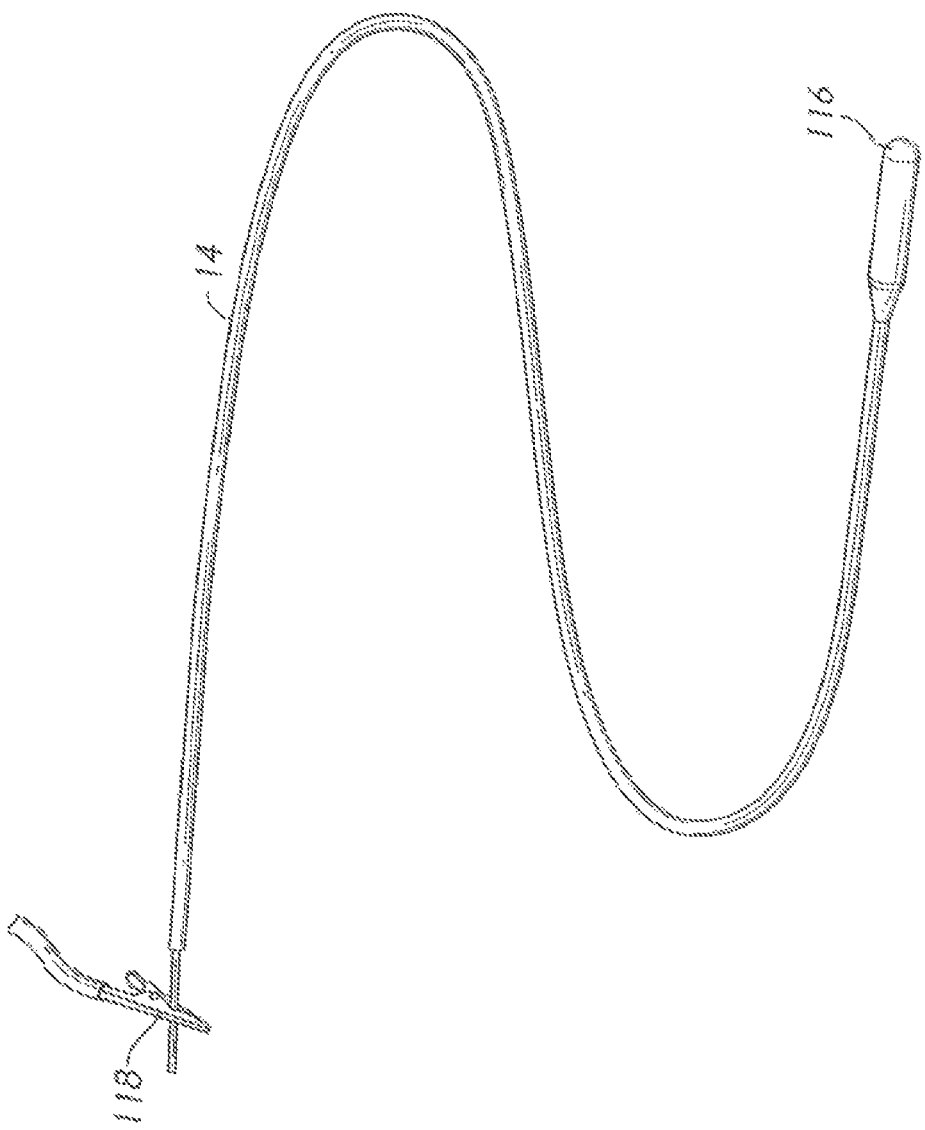
FIG. 9 is a perspective view, showing a guide wire made according to the present invention.

FIG. 9 provides a perspective view of the inventive guide wire 14 as a whole (Note that the diameter is again shown significantly greater than the actual device in order to aid visualization). The guide wire can be produced in different lengths and the overall length of the guide wire will typically be much greater than is shown in the example in the view. Exposed portion 116 is located on the very distal end of the guide wire. Another region that is free of insulating coating is provided on the proximal end. Electrical lead 118 is attached to this proximal exposed region, typically by clamping the electrical lead to the core wire. The result is a low-resistance conductive path between electrical lead 118 and exposed portion 116. Electrical lead 118 is then connected to a prior art catheter mapping and navigation system.

Figure 5:
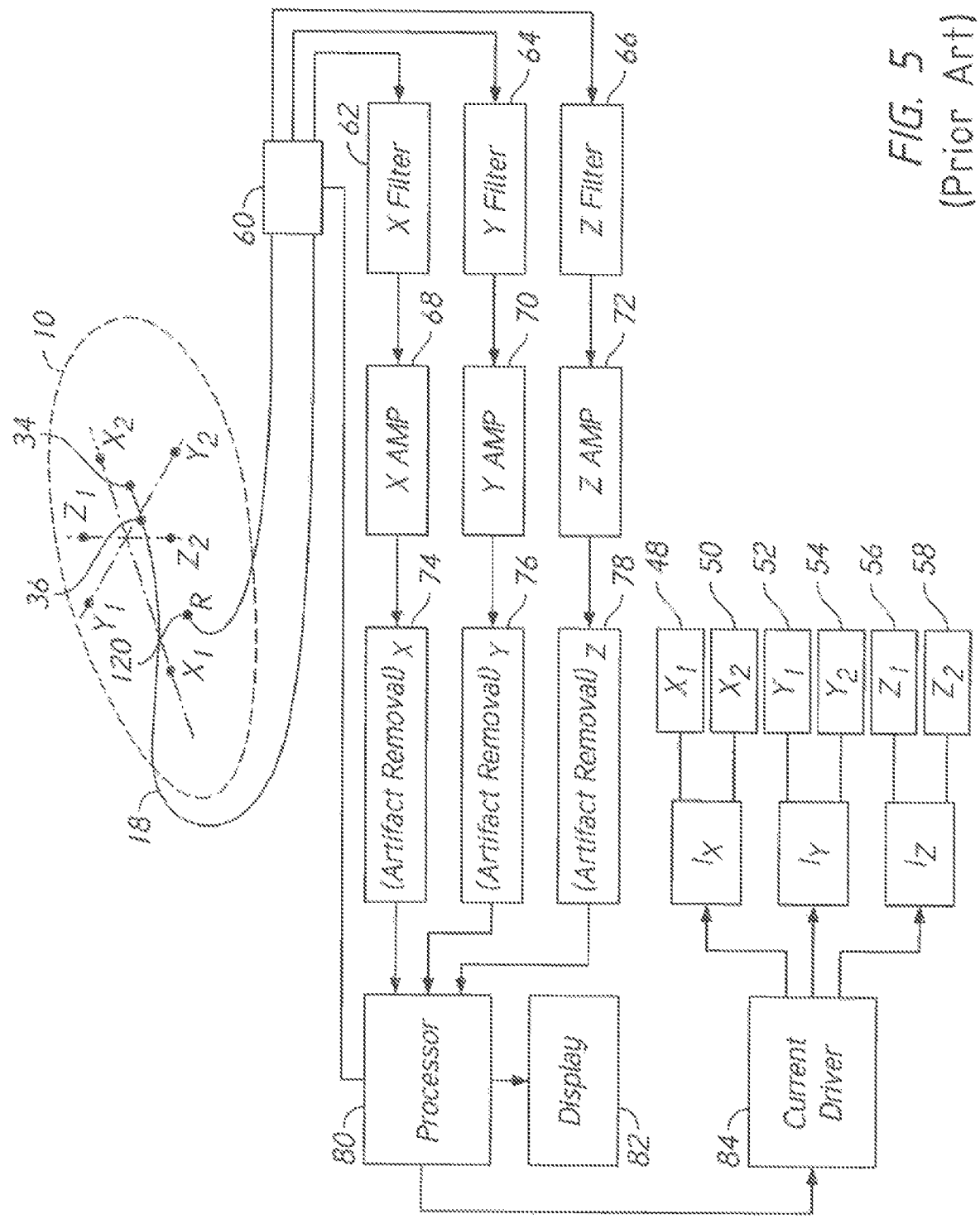
FIG. 5 is a schematic view, showing exemplary equipment used for catheter navigation and mapping.
Figure 6:
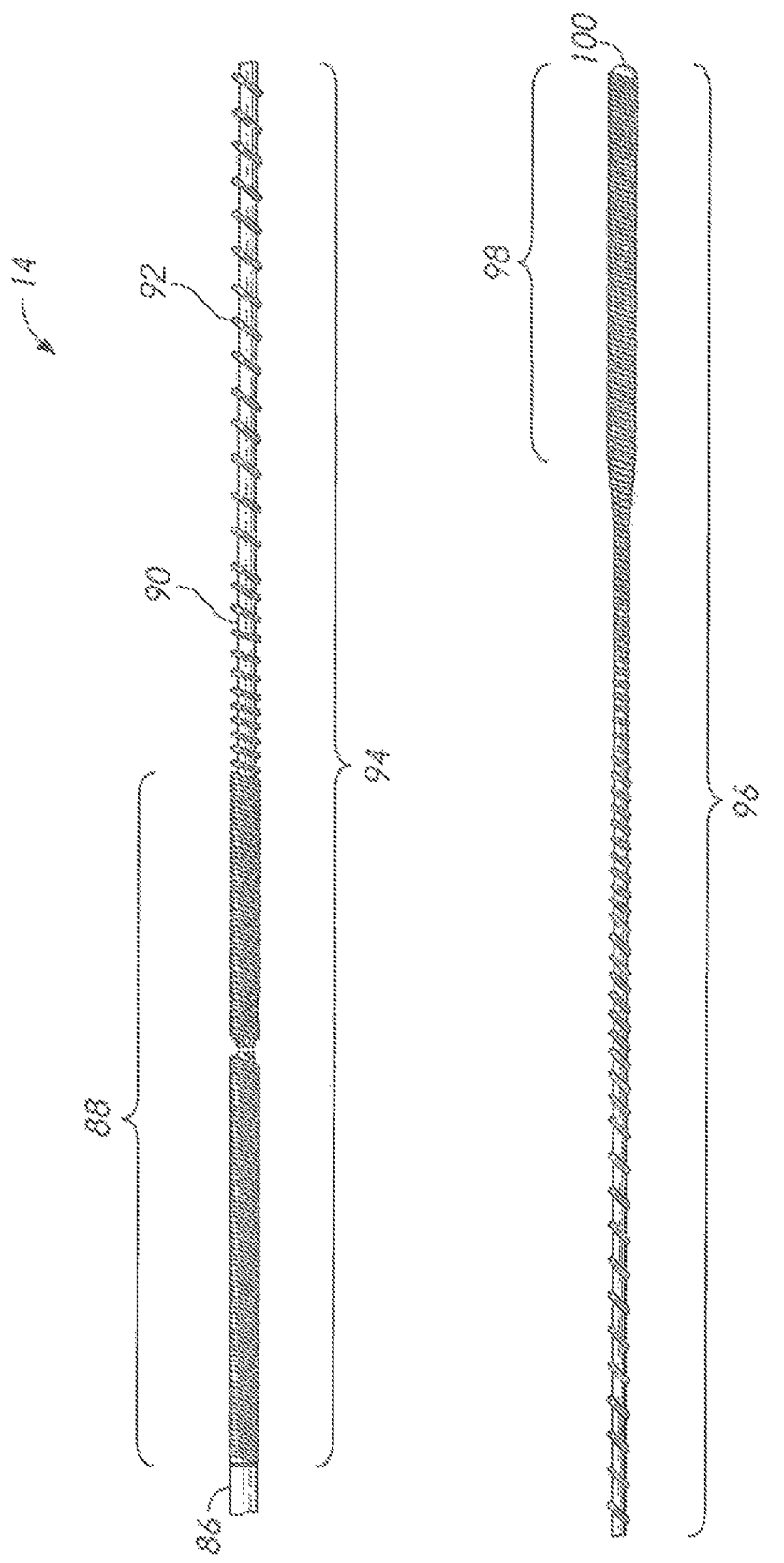
FIG. 6 is an elevation view, showing an exemplary prior art guide wire.
Figure 7:
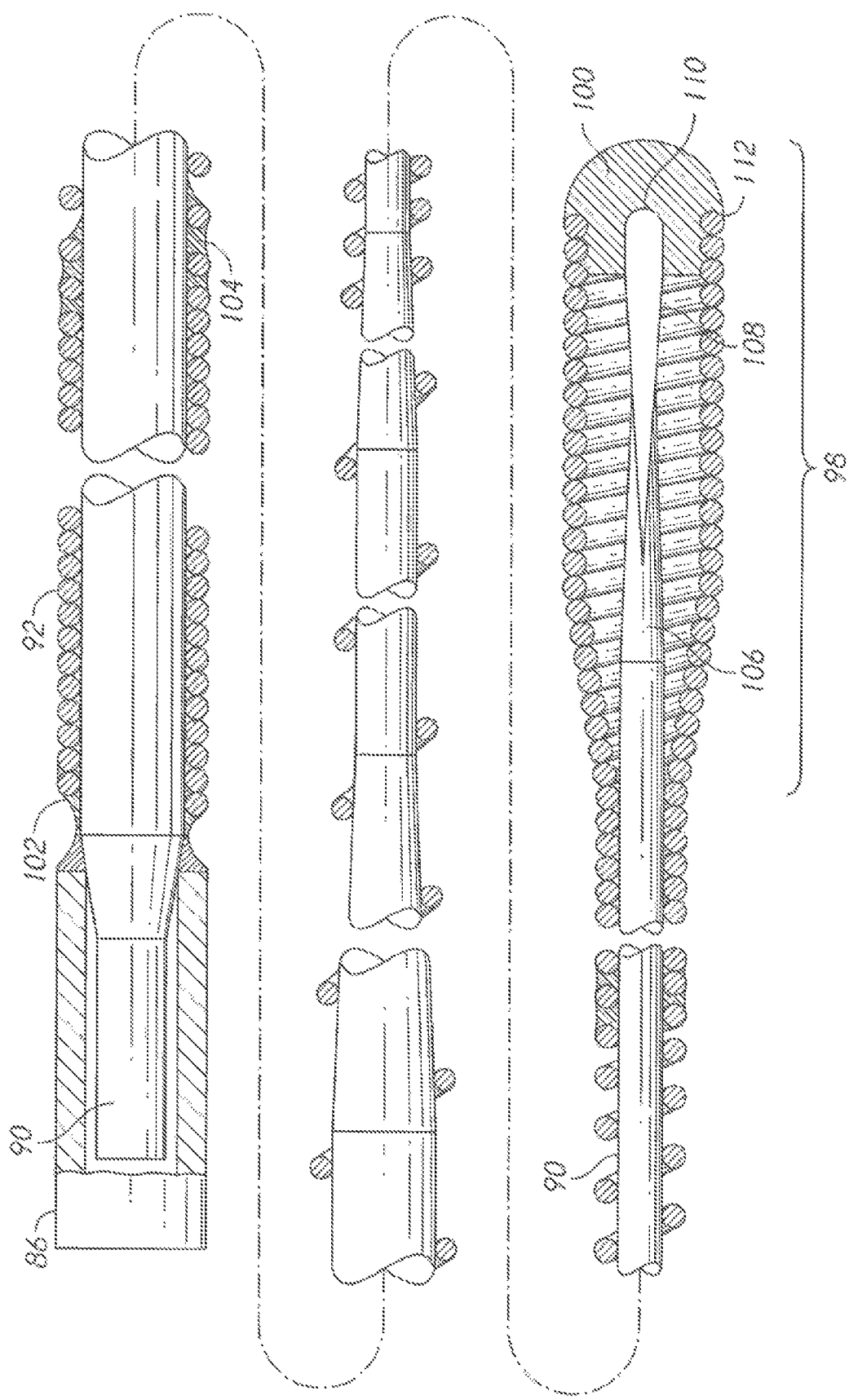
FIG. 7 is a partial sectional view, showing an exemplary prior art guide wire.
Figure 10:
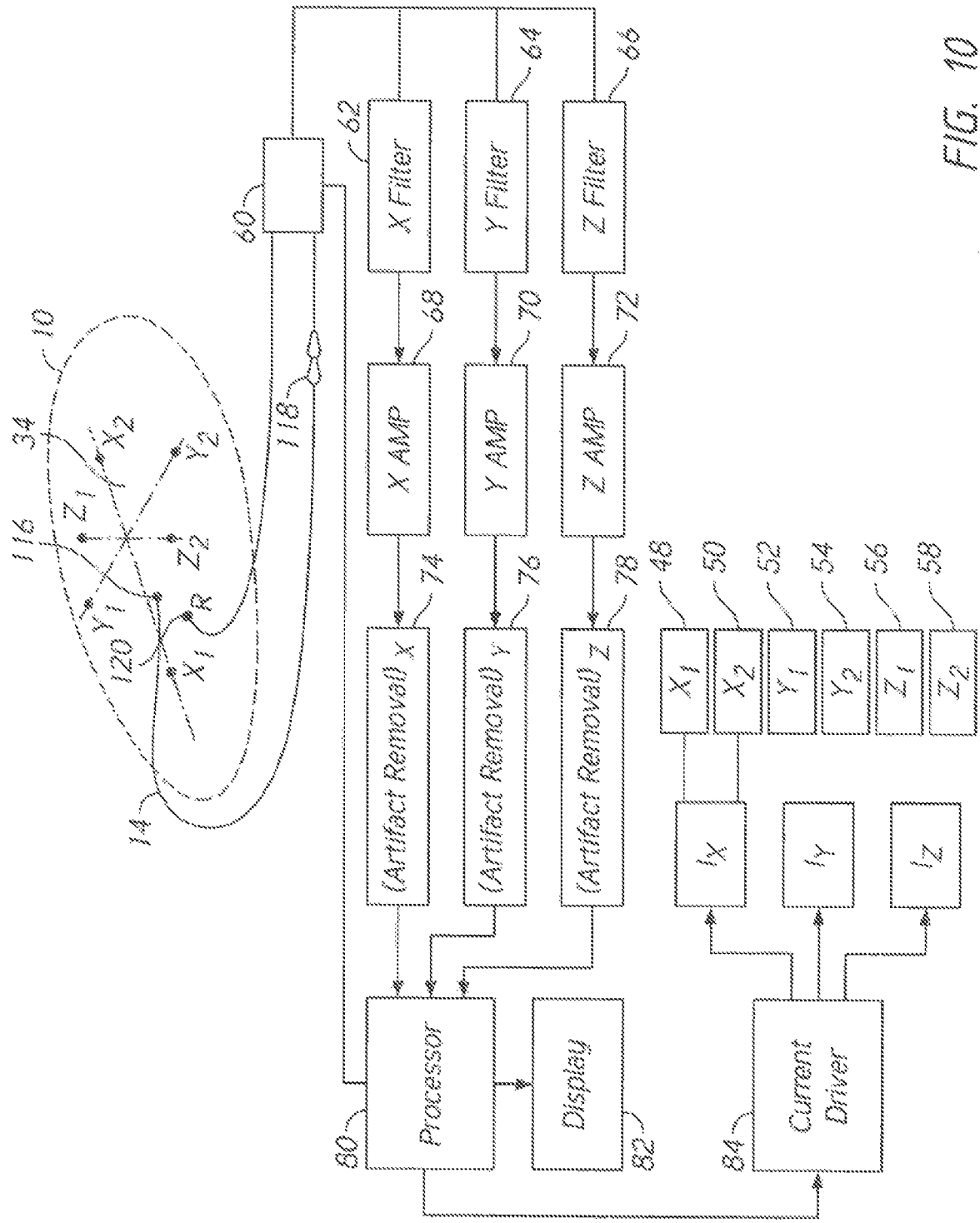
FIG. 10 is a schematic view, showing exemplary equipment used for navigation and mapping of the present inventive guide wire.

FIG. 10 shows a catheter mapping and navigation system that is the same as the system depicted in FIG. 5, except that guide wire 14 is now connected via electrical lead 118 (Other components—such as a catheter that is already in the patient—may be connected as well, but they are not shown in the view for purposes of visual clarity). The positional processing carried out by the system is the same as for a prior art catheter depicted in FIG. 5. The channel processors evaluate a measured voltage between exposed portion 116 and reference electrode 120. This measured voltage is evaluated for the X-axis, the Y-Axis, and the Z-axis. The position of exposed portion 116 within the patient is thereby determined in real-time.

Figure 11:
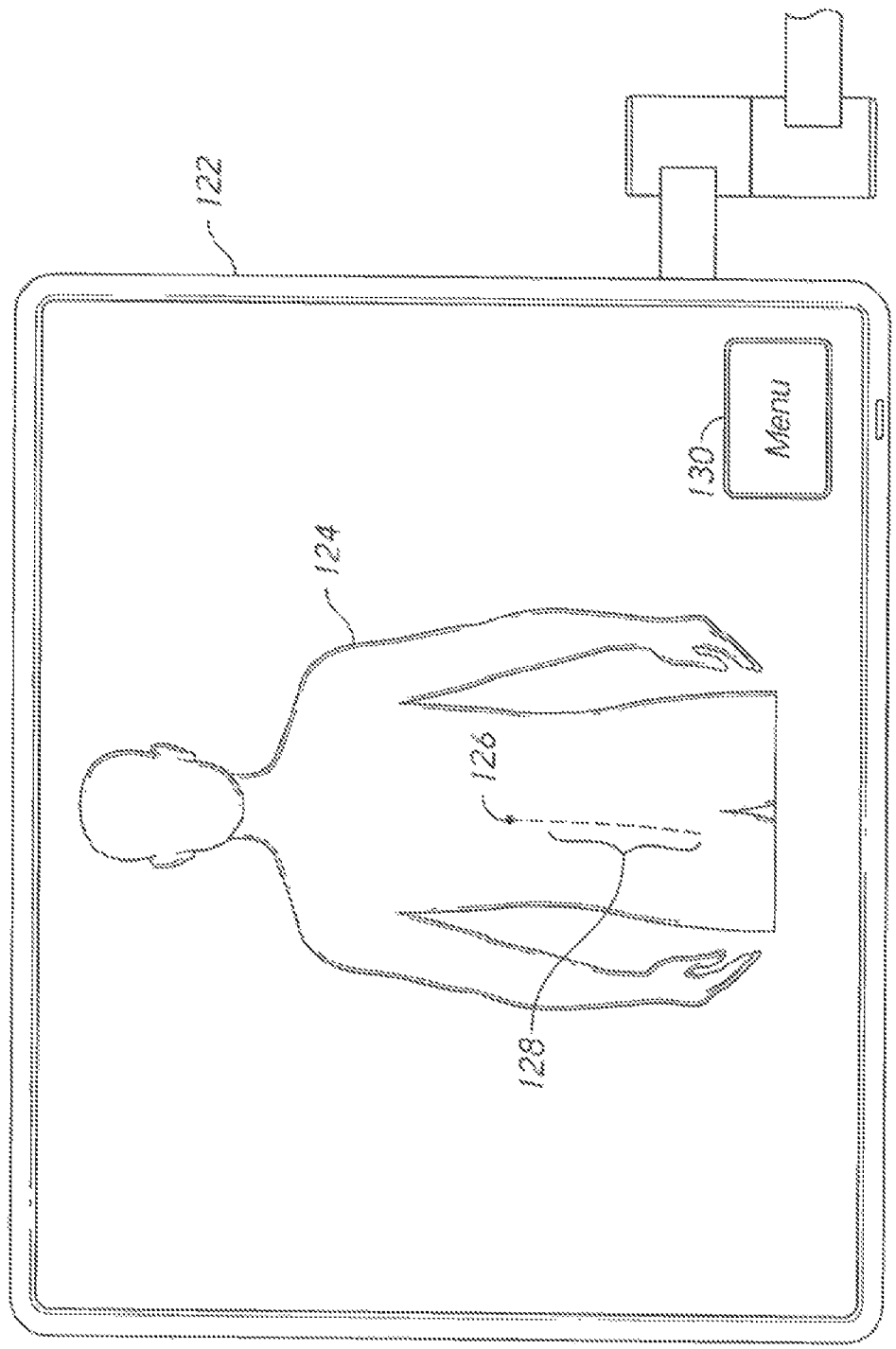
FIG. 11 is an elevation view, showing an exemplary depiction of the inventive guide wire on a video monitor.
Figure 12:
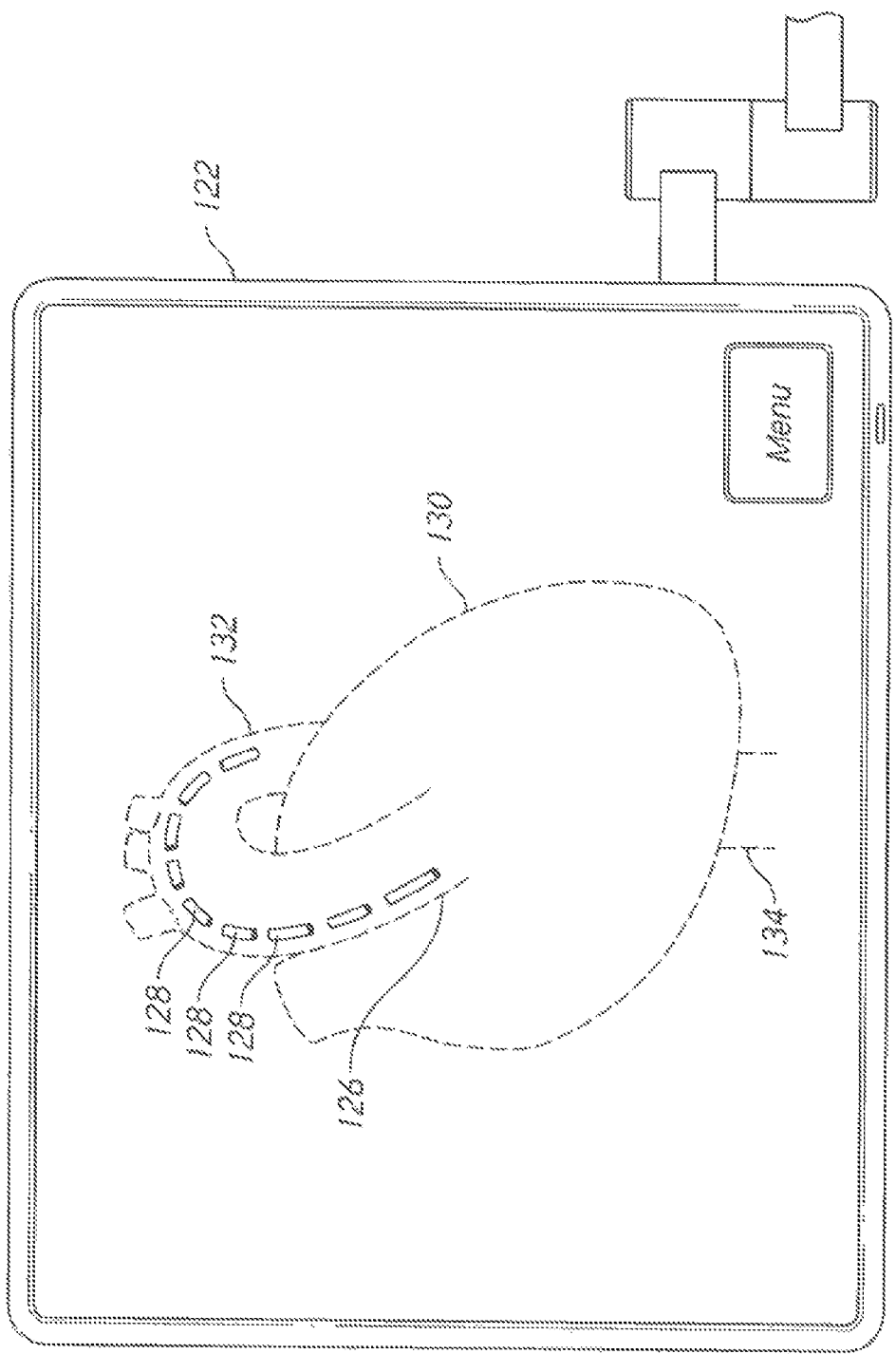
FIG. 12 is an elevation view, showing an exemplary depiction of the inventive guide wire on a video monitor.
Figure 13:
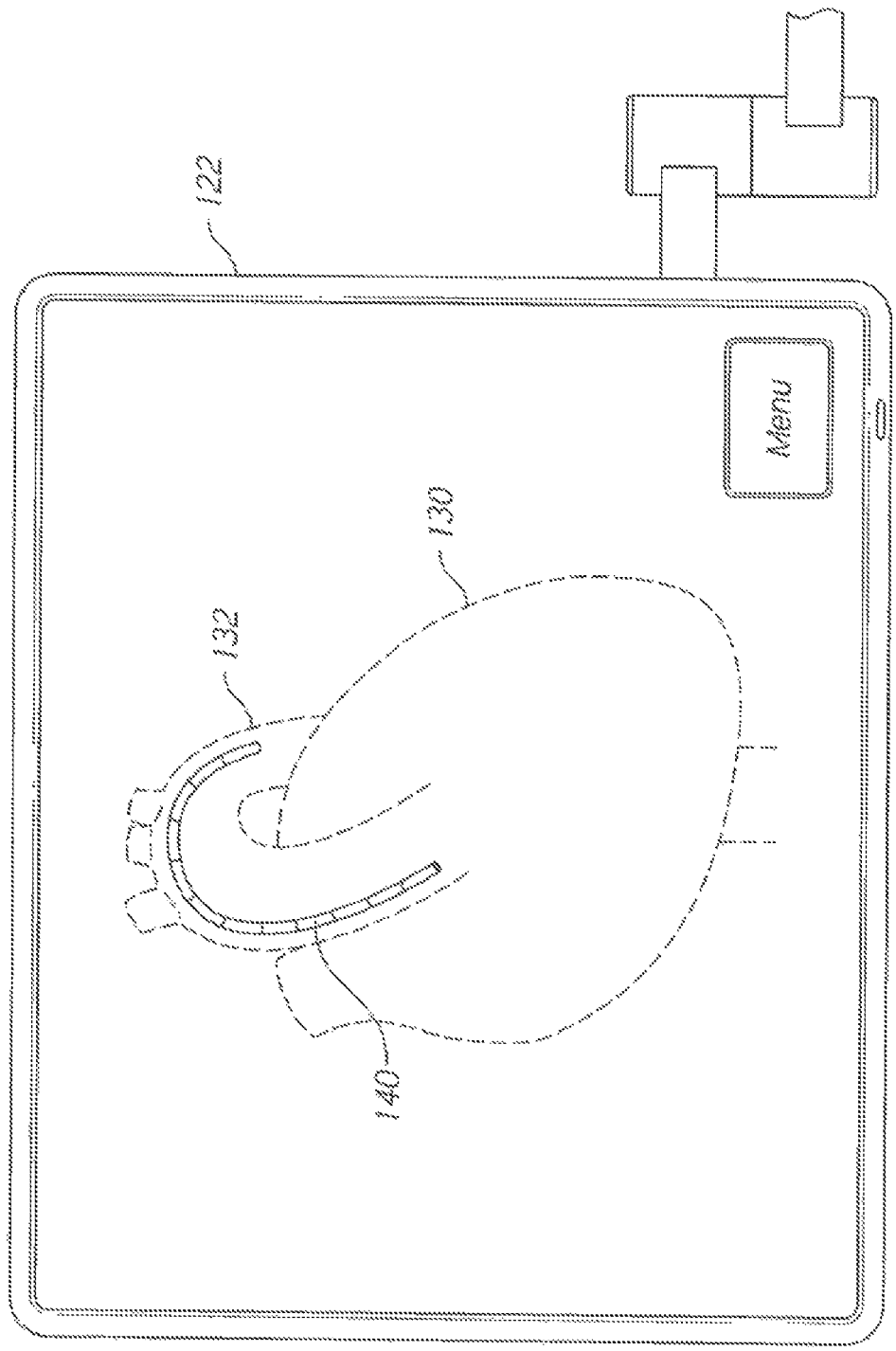
FIG. 13 is an elevation view, showing an exemplary depiction of the inventive guide wire on a video monitor.

The position of the exposed portion is continually updated as the guide wire is advanced within the patient (including filtering, amplifying, artifact removal, etc.). As for the prior art display of a catheter, processor 80 develops and transmits display information to display 82. The display information can be presented to the physician in many different ways FIGS. 11-13 provide a simplified depiction of an exemplary display. In FIG. 11, patient depiction 124 is provided on monitor 122. Touch-based menu 130 is also provided on the monitor, The menu preferably allows the physician to pan, zoom, and reorient the patient depiction. Since the available position data is three-dimensional, it can be displayed in any desired orientation.

In the example shown tip location 126 is depicted as a bright cylinder. Route history depiction 128 is a "ghosted" display of every prior location the system has determined for the exposed portion. The route history depiction allows the physician to visualize the progress of the guide wire through the patient's body.

In this example the physician is feeding a guide wire into the left ventricle. In FIG. 12, the physician has zoomed in on the region of the heart to visualize the passage of the guide wire through the aortic arch. Tip location depiction 126 is again depicted as a bright cylinder. Its size is increased to reflect the increased level of zoom selected. Route history depiction 128 is also shown.

As those skilled in the art will know, the processing software used with the prior art catheter mapping and navigation systems is able to depict anatomical structures and enhance the depiction as more and more data points are harvested. In the example of FIG. 12, it is significant to note that the passage of the guide wire up the descending aorta and through the aortic arch provides a good reference scheme for the structures of the heart. The software uses this reference scheme to create simplified depictions such as descending aorta depiction 134, heart depiction 130, and aortic arch depiction 132. These references assist the physician in maintaining situational awareness.

There are many possible methods of depicting the advancing guide wire. FIG. 13 presents an alternate method. In this approach 3D depiction 140 is provided. The 3D depiction is a 2D projection (on the monitor) of a 3D object created in software. The 3D object is created as a swept constant cross-section. The cross-section is simply the circular cross section of the guide wire. It is swept along a spline that passes through all the points that have been calculated for the exposed portion. Once the spline is created a more complex shape can be created for the 3D object. As an example, the enlarged diameter for end portion 98 of the guide wire can be shown as part of the 3D depiction.

Figure 14:
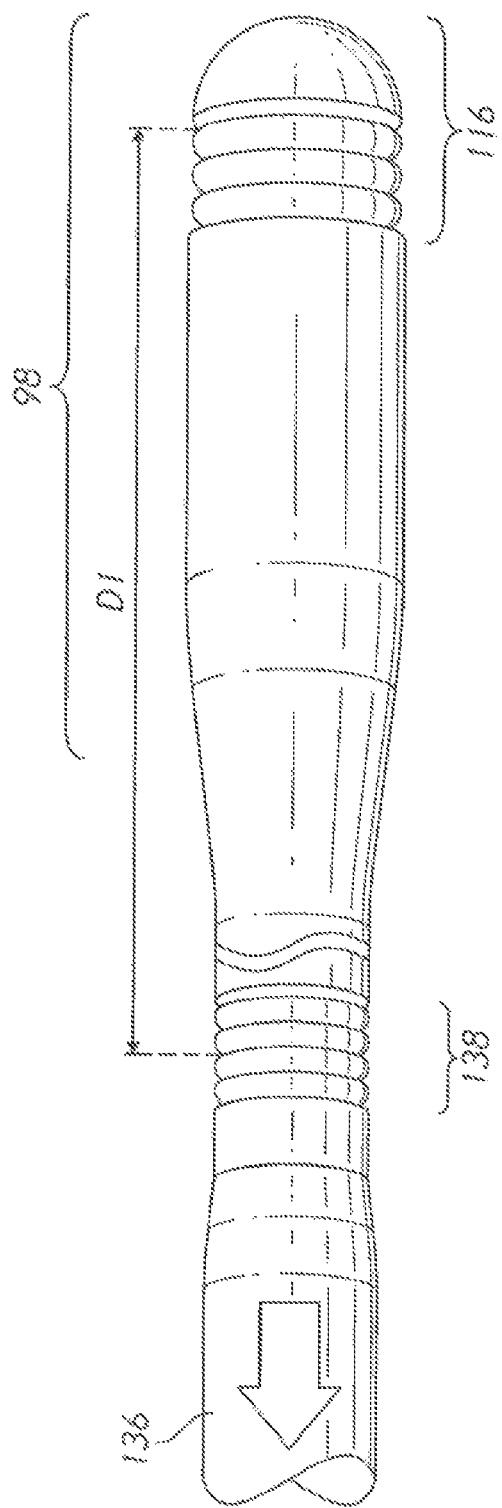
FIG. 14 is a perspective view, showing an additional embodiment of the inventive guide wire.

Additional enhancements can be provided for the inventive guide wire. FIG. 14 shows an alternate version of the guide wire in which exposed region 138 is provided some distance away from exposed portion 116. Multiple exposed regions can, be provided along the length of the guide wire. These exposed regions are simply areas where the electrically insulating coating of the guide wire is exposed. The helical coil is visible in the exposed regions 138,116. The distance "D1" between the exposed regions 116,138 is somewhat arbitrary, and can be selected to provide desired guidance for the physician. In the preferred embodiments the distance "D1" lies between about 75 mm (3 inches) and about 250 mm (10 inches).

The reader should bear in mind that the helical coil within exposed region 138 is the same as that exposed within exposed portion 116. Thus, there is essentially a zero-resistance connection between the two exposed regions. The effect of this connection is that the catheter mapping and navigation system only senses a position of the more proximal of the two exposed regions (and even this may be skewed by the creation of a zero-resistance current path through the guide wire).

In this version insulating sheath 136 is provided over the coating on the guide wire. The physician is able to withdraw this insulating sheath while leaving the guide wire in position. The initial position of the insulating sheath covers exposed region 138, meaning that exposed region 138 is not visible on the catheter mapping and navigation system. When insulating sheath 136 is withdrawn in the direction indicated by the arrow, exposed region 138 becomes visible but exposed portion 116 becomes invisible. If additional exposed regions are provided down the length of the guide wire, the withdrawal of insulating sheath 136 will cause each more proximal exposed region ("more proximal" meaning closer to entry site 12) to be displayed on the navigation and mapping system (though only one will be displayed at a time).

After insulating sheath 136 is removed the physician advances a catheter over the guide wire. The advancing catheter will electrically insulate each exposed portion of the guide wire it passes over. Each successive exposed region of the guide wire will "wink out" on the mapping and navigation display as the catheter passes over it. When a particular exposed region "winks out" the next more distal exposed region will appear on the navigation display and it will remain until the catheter passes over it. In this way the physician can monitor the progress of the catheter advancing over the guide wire. In practice the provision of the two exposed regions 116,138 is sufficient and this represents the preferred embodiment.

Figure 15:
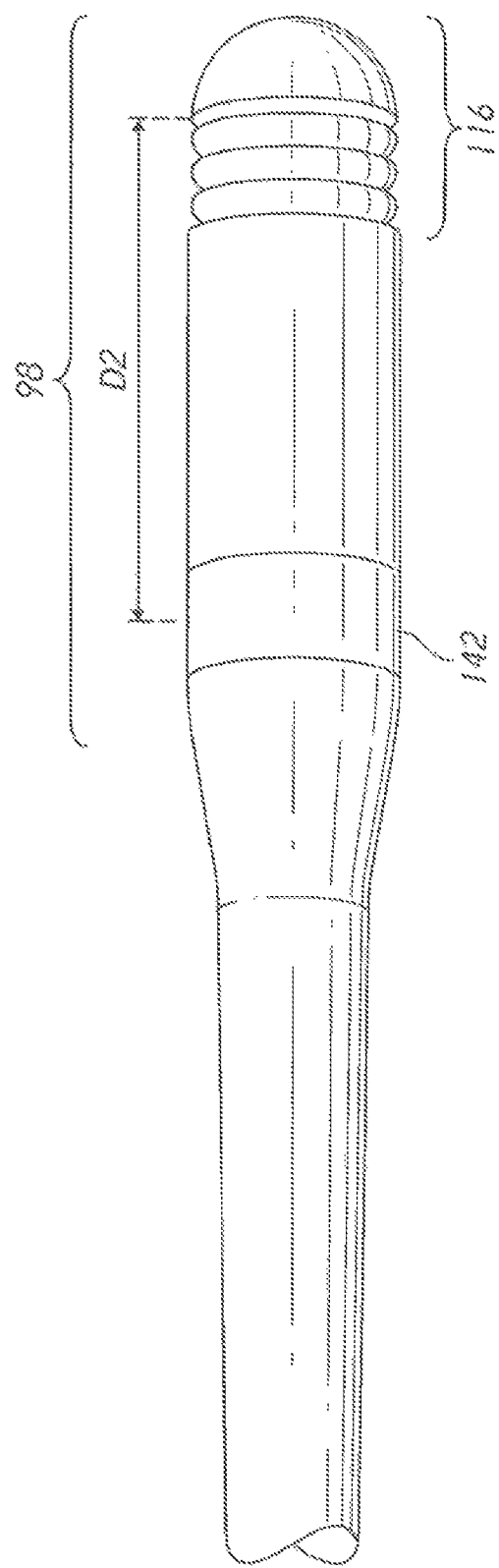
FIG. 15 is a perspective view, showing an additional embodiment of the inventive guide wire.
Figure 16:
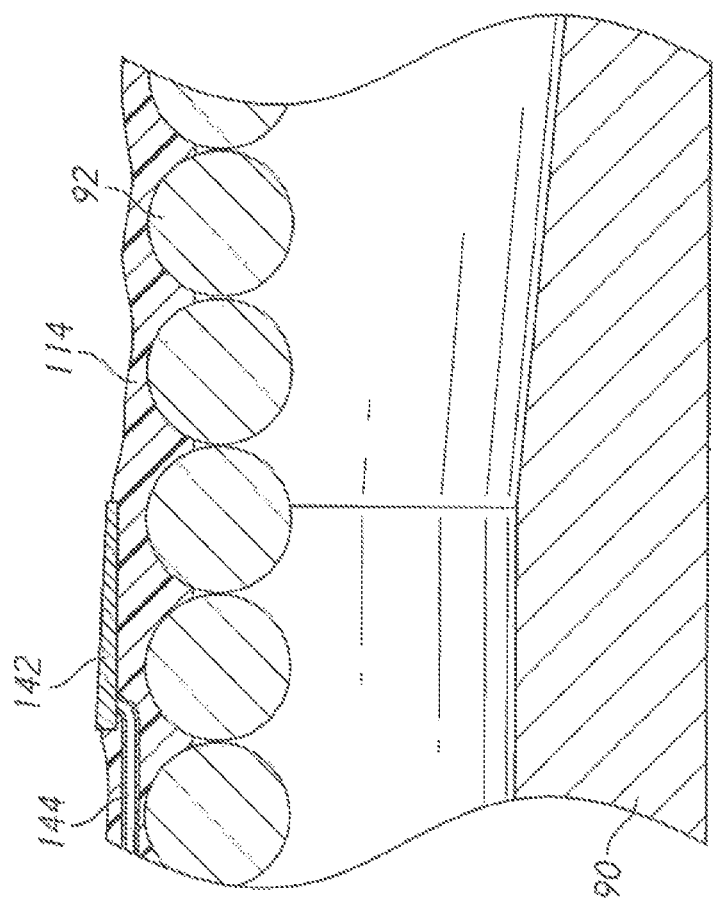
FIG. 16 is a sectional view, showing internal details of the embodiment of FIG. 15.

FIGS. 15 and 16 illustrate an alternate embodiment that adds additional complexity but also provides additional functionality. Exposed portion 116 is provided as for the prior example. Secondary electrode 142 is also provided. FIG. 16 shows a sectional view through the outer surface of the guide wire in the region of secondary electrode 142. The secondary electrode is provided on the outer surface of coating 114. Insulated lead 144 is connected to the secondary electrode. This insulated lead travels all the way to the proximal region of the guide wire (the portion lying outside the patient's body). The reader will note that secondary electrode 142 is electrically insulated from the exposed portion 116. The catheter mapping and navigation system is connected to the metallic components of the guide wire as explained previously (typically by clipping a lead to an exposed portion on the proximal end of the guide wire). Secondary electrode 142 is electrically connected to the mapping and navigation system by clipping a separate lead to insulated lead 144.

Returning to FIG. 15, those skilled in the art will appreciate that providing a secondary electrode 142 creates effectively a two-electrode system (exposed portion 116 and secondary electrode 142). If these two components are spaced a known distance "D2" apart, then the calibration techniques described for the prior art mapping and navigation systems can be employed to increase the accuracy of the position calculations. However, those skilled in the art will know that guide wires have a very small diameter and the provision of a secondary electrode and secondary conductive path will be quite difficult. For these reasons, the alternate embodiment shown in FIGS. 15 and 16 is not preferred.

Figure 17:
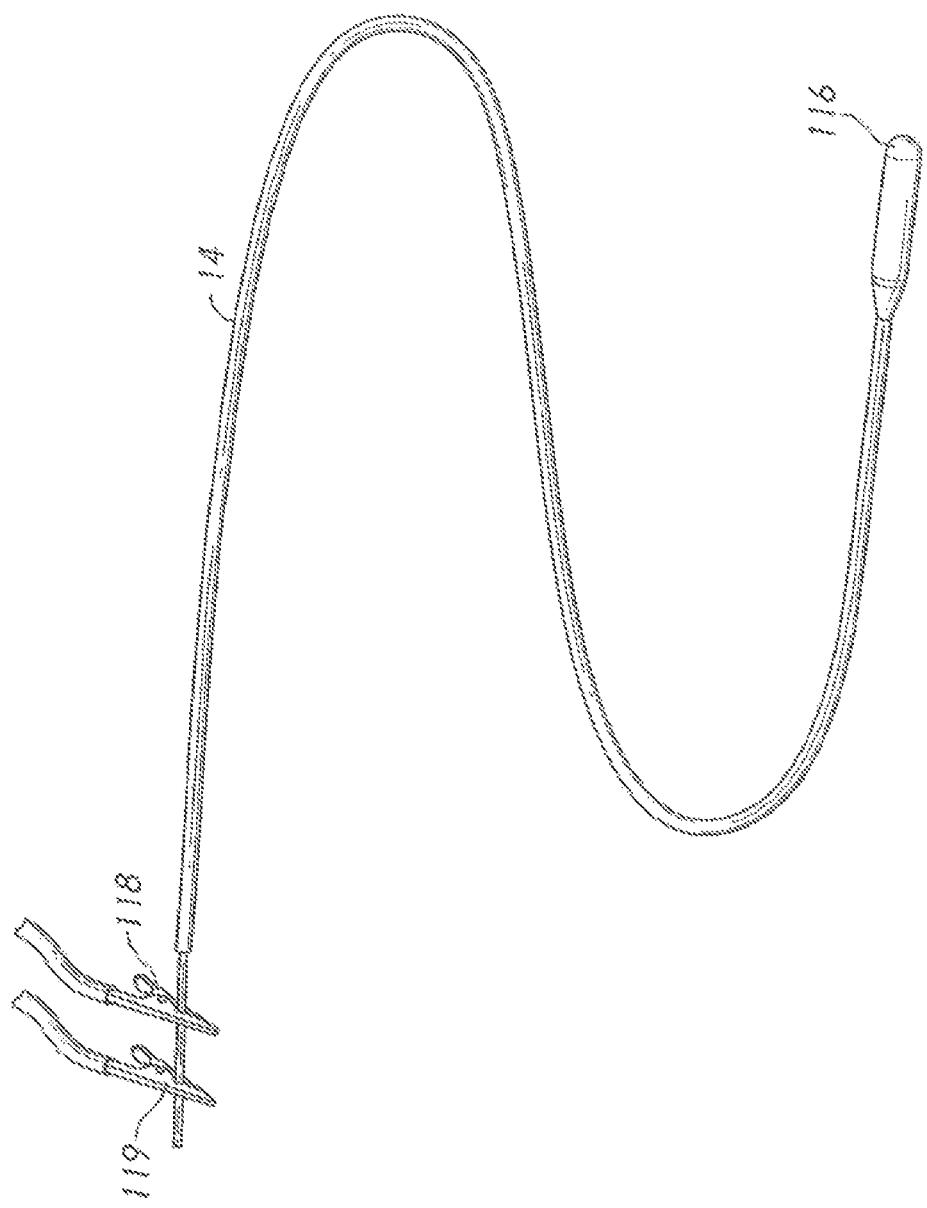
FIG. 17 is a perspective view, showing the use of two electrical leads attached to the inventive guide wire.

FIG. 17 provides a perspective view of the inventive guide wire 14 including exposed portion 116 on its distal tip. As for the example shown in FIG. 9, an electrode 118 has been clipped to the exposed portion of the guide wire at the proximal end. The reader will note that a second electrode 119 has also been clipped to the same exposed portion of the guide wire. The example of FIG. 9 is a unipolar configuration. The example of FIG. 17 is a bipolar configuration. Electrode 118 is the positive lead for the catheter mapping system and electrode 119 is the corresponding negative lead. One might naturally expect this configuration to create a dead short between the two leads and thereby eliminate the display of the location of exposed portion 116 on the navigation and mapping system monitor. However, experimentation has shown that the use of both the positive and negative leads actually increases accuracy and does not inhibit the determination of the position of exposed portion 116. Thus, it is possible to operate the inventive guide wire in either a unipolar or a bipolar configuration.

The inventive systems thus described can include many other features and combinations of features. These include:
1. Providing multiple additional electrodes (such as secondary electrode 142) along the length of the guide wire, with all of these electrodes being connected separately to the mapping and navigation system.
2. The inventive system can be combined with prior art fluoroscopy, and the visual depiction of the guidewire tip can be laid over a fluoroscopic image. The guide wire materials can be selected to provide radio opacity for this purpose.
3. The inventive system can be used in combination with an electrode-equipped catheter. The presence of additional electrodes tends to enhance the accuracy of the prior art mapping and navigation systems. If a catheter is already present it may be used to enhance the accuracy of a guide wire that is being introduced for an additional procedure.

Although the preceding description contains significant detail, it should not be construed as limiting the scope of the invention but rather as providing illustrations of the preferred embodiments of the invention. Those skilled in the art will be able to devise many other embodiments that carry out the present invention. Thus, the language used in the claims shall define the invention rather than the specific embodiments provided.

Having described my invention, I claim:

1. A method for displaying the position of a guide wire within a patient, comprising:
   (a) providing a mapping and navigation system, including,
      (i) an X1 electrode and an X2 electrode, configured to pass an electrical current through said patient along an X axis between said X1 electrode and said X2 electrode,
      (ii) a Y1 electrode and a Y2 electrode, configured to pass an electrical current through said patient along a Y axis between said Y1 electrode and said Y2 electrode,
      (iii) a Z1 electrode and a Z2 electrode, configured to pass an electrical current through said patient along a Z axis between said Z1 electrode and said Z2 electrode,
      (iv) voltage measurement equipment configured to measure a voltage between an electrode within said patient and a reference electrode,
      (v) a processor configured to convert said measured voltage between said electrode within said patient and said reference electrode into location information along said X axis, said Y axis, and said Z axis—whereby said location information includes a position of said electrode within said patient in three-dimensional space,
      (vi) a display for visually displaying said location information;
   (b) providing a guide wire having a proximal end and a distal end, including,
      (i) an electrically conductive core wire,
      (ii) an electrically conductive helical coil,
      (iii) an electrically insulating coating over said guide wire;
   (c) providing an exposed portion within said distal end of said guide wire, said exposed portion acting as said electrode within said patient when said distal end of said guide wire is inserted into said patient;
   (d) electrically connecting said voltage measuring equipment to said proximal end of said guide wire;
   (e) while said distal end of said guide wire is within said patient, using said X1, X2, Y1, Y2, Z1, and Z2 electrodes to pass an electrical current through said patient and using said voltage measuring equipment to repeatedly measure a voltage between said exposed portion and said reference electrode;
   (f) advancing said distal end of said guide wire through said patient along a curving path;
   (g) repeatedly using said processor to convert said measured voltages between said exposed portion and said reference electrode into location information for said exposed portion along said X axis, said Y axis, and said Z axis—whereby said location information includes a position of said electrode within said patient in three-dimensional space;
   (h) repeatedly updating and displaying said location information for said exposed portion on said display as said distal end of said guide wire is advanced through said patient;
   (i) providing an electrically insulating catheter that is a sliding fit over said guide wire;
   (j) advancing said insulating catheter over said guide wire and into said patient; and
   (k) wherein said exposed portion is electrically insulated from said patient as said insulating catheter advances over said exposed portion, thereby causing said display of said location information for said exposed portion to change as said insulating catheter advances over said exposed portion.

2. A method for displaying the position of a guide wire within a patient as recited in claim 1, wherein said core wire and said helical coil are configured to deflect a tip of said guide wire when said helical coil is rotated with respect to said core wire.

3. A method for displaying the position of a guide wire within a patient as recited in claim 2, wherein said electrically insulating coating on said guide wire also provides a low surface friction.

4. A method for displaying the position of a guide wire within a patient as recited in claim 2, wherein said guide wire is also radio opaque.

5. A method for displaying the position of a guide wire within a patient as recited in claim 2, further comprising:
  (a) providing a second exposed portion on said guide wire that is separated from said first exposed portion;
  (b) while said distal end of said guide wire is within said patient, using said voltage measuring equipment to measure a voltage between said second exposed portion and said reference electrode;
  (c) using said processor to convert said measured voltage between said second exposed portion and said reference electrode into location information for said second exposed portion along said X axis, said Y axis, and said Z axis—whereby said location information includes a position of said second exposed portion within said patient in three-dimensional space; and
  (d) displaying said location information for said second exposed portion on said display.

6. A method for displaying the position of a guide wire within a patient as recited in claim 5, further comprising providing an electrically insulating sheath configured to selectively cover said second exposed portion.

7. A method for displaying the position of a guide wire within a patient as recited in claim 1, further comprising displaying both present and past location information for said exposed portion so that progress of said exposed portion through said patient can be visualized.

8. A method for displaying the position of a guide wire within a patient as recited in claim 1, wherein said guide wire is also radio opaque.

9. A method for displaying the position of a guide wire within a patient as recited in claim 1, further comprising:
  (a) providing a second exposed portion on said guide wire that is separated from said exposed portion in the proximal direction, with said exposed portion and said second exposed portions being electrically connected by said guide wire;
  (b) providing a removable insulating sheath over said guide wire; and
  (c) before advancing said insulating catheter over said guide wire, removing said insulating sheath in the proximal direction, whereby said second exposed portion becomes electrically coupled to said patient and said display of said location information changes from a display of said location information for said exposed portion to a display of said location information for said second exposed portion.

10. A method for displaying the position of a guide wire within a patient as recited in claim 9, further comprising:
  (a) advancing said insulating catheter over said second exposed portion and toward said exposed portion; and
  (b) whereby said second exposed portion becomes electrically insulated from said patient and said display of said location information changes from a display of said location information for said second exposed portion to a display of said location information for said exposed portion.

11. A method for displaying the position of a guide wire within a patient, comprising
  (a) providing a mapping and navigation system, including,
    (i) an X1 electrode and an X2 electrode, configured to pass an electrical current through said patient along an X axis between said X1 electrode and said X2 electrode,
    (ii) a Y1 electrode and a Y2 electrode, configured to pass an electrical current through said patient along a Y axis between said Y1 electrode and said Y2 electrode,
    (iii) a Z1 electrode and a Z2 electrode, configured to pass an electrical current through said patient along a Z axis between said Z1 electrode and said Z2 electrode,
    (iv) voltage measurement equipment configured to measure a voltage of an electrode within said patient,
    (v) a processor configured to convert said measured voltage between said electrode within said patient into a position in three-dimensional space,
    (vi) a display for visually displaying said position;
  (b) providing a guide wire having a proximal portion and a distal portion, including,
    (i) an electrically conductive core wire,
    (ii) an electrically conductive helical coil that is electrically connected to said conductive core wire,
    (iii) an electrically insulating coating over said guide wire;
  (c) providing an exposed portion within said distal end of said guide wire, said exposed portion acting as said electrode within said patient when said distal portion of said guide wire is inserted into said patient;
  (d) electrically connecting said voltage measuring equipment to said proximal portion of said guide wire;
  (e) while said distal portion of said guide wire is within said patient, using said X1, X2, Y1, Y2, Z1, and Z2 electrodes to pass an electrical current through said patient and using said voltage measuring equipment to repeatedly measure a voltage of said exposed portion;
  (f) advancing said distal portion of said guide wire through said patient;
  (g) repeatedly using said processor to convert said measured voltages of said exposed portion into a position of said exposed portion in three-dimensional space;
  (h) repeatedly updating and displaying said position for said exposed portion on said display as said distal end of said guide wire is advanced through said patient;
  (i) providing an electrically insulating catheter that is a sliding fit over said guide wire;
  (j) advancing said insulating catheter over said guide wire and into said patient; and
  (k) wherein said exposed portion is electrically insulated from said patient as said insulating catheter advances over said exposed portion, thereby causing said display of said location information for said exposed portion to change as said insulating catheter advances over said exposed portion.

12. A method for displaying the position of a guide wire within a patient as recited in claim 11, wherein said core wire and said helical coil are configured to deflect a tip of said guide wire when said helical coil is rotated with respect to said core wire.

13. A method for displaying the position of a guide wire within a patient as recited in claim 12, wherein said electrically insulating coating on said guide wire also provides a low surface friction.

14. A method for displaying the position of a guide wire within a patient as recited in claim 12, wherein said guide wire is also radio opaque.

15. A method for displaying the position of a guide wire within a patient as recited in claim 12, further comprising:
   (a) providing a second exposed portion on said guide wire that is separated from said first exposed portion;
   (b) while said distal portion of said guide wire is within said patient, using said voltage measuring equipment to measure a voltage of said second exposed portion;
   (c) using said processor to convert said measured voltage for said second exposed portion to a position for said second exposed portion along said X axis, said Y axis, and said Z axis—whereby said location information includes a position of said second exposed portion within said patient in three-dimensional space; and
   (d) displaying said position for said second exposed portion on said display.

16. A method for displaying the position of a guide wire within a patient as recited in claim 15, further comprising providing an electrically insulating sheath configured to selectively cover said second exposed portion.

17. A method for displaying the position of a guide wire within a patient as recited in claim 11, further comprising displaying both present and past location information for said exposed portion so that progress of said exposed portion through said patient can be visualized.

18. A method for displaying the position of a guide wire within a patient as recited in claim 11, wherein said guide wire is also radio opaque.

19. A method for displaying the position of a guide wire within a patient as recited in claim 11, further comprising:
   (a) providing a second exposed portion on said guide wire that is separated from said exposed portion in the proximal direction, with said exposed portion and said second exposed portions being electrically connected by said guide wire;
   (b) providing a removable insulating sheath over said guide wire; and
   (c) before advancing said insulating catheter over said guide wire, removing said insulating sheath in the proximal direction, whereby said second exposed portion becomes electrically coupled to said patient and said display of said location information changes from a display of said location information for said exposed portion to a display of said location information for said second exposed portion.

20. A method for displaying the position of a guide wire within a patient as recited in claim 19, further comprising:
   (a) advancing said insulating catheter over said second exposed portion and toward said exposed portion; and
   (b) whereby said second exposed portion becomes electrically insulated from said patient and said display of said location information changes from a display of said location information for said second exposed portion to a display of said location information for said exposed portion.

* * * * *